(12) United States Patent
Fusco

(10) Patent No.: US 6,616,619 B2
(45) Date of Patent: Sep. 9, 2003

(54) DIAGNOSTIC AND THERAPEUTIC METHOD FOR IDENTIFICATION AND TREATMENT OF POSTURAL DISTURBANCES

(76) Inventor: Maria Antonietta Fusco, Viale S. Francesco 32 int. 138-A, sc. A, Avellino, AV 83100 (IT)

( * ) Notice: Subject to any disclaimer, the term of this patent is extended or adjusted under 35 U.S.C. 154(b) by 0 days.

(21) Appl. No.: 09/973,591

(22) Filed: Oct. 8, 2001

(65) Prior Publication Data

US 2003/0069524 A1 Apr. 10, 2003

(51) Int. Cl.$^7$ .......................... A61B 5/103; A61B 5/117
(52) U.S. Cl. .................. 600/587; 600/592; 600/594
(58) Field of Search ................... 600/587, 300, 600/592, 594, 595; 351/200

(56) References Cited

U.S. PATENT DOCUMENTS 6,443,572 B1 * 9/2002 Lawson ...................... 351/203

FOREIGN PATENT DOCUMENTS

AU        B-43651/97        7/1998

OTHER PUBLICATIONS

Fusco, Maria Antonietta M.D, Ph.D. Textbook and Atlas of Plantar Posturology. Mar. 2000, Scuderi Editrice—Italy.*

* cited by examiner

*Primary Examiner*—Max F. Hindenburg
*Assistant Examiner*—Jonathan Foreman
(74) *Attorney, Agent, or Firm*—Leffert Jay & Polglaze, P.A.

(57) ABSTRACT

A method for etiologic diagnosis of ascending postural disturbances and a therapeutic method for correction of such ascending postural disturbances, comprising the steps of: identifying the type of a patient's postural disturbance to ascertain whether it is of an ascending, descending or multiple type, by means of mechanical maneuvers each apt to inhibit a respective foot or cranial nervous input to the Central Nervous System; in case an ascending postural disturbance is identified, identifying the specific intrinsic muscle(s) of the foot sole responsible for such disturbance; and performing an exteroceptive, pressoceptive, proprioceptive and/or reflexogen stimulation of an insertion point of the intrinsic muscle(s) identified as responsible for the ascending postural disturbance.

10 Claims, No Drawings

DIAGNOSTIC AND THERAPEUTIC METHOD FOR IDENTIFICATION AND TREATMENT OF POSTURAL DISTURBANCES

FIELD OF THE INVENTION

The present invention relates to a diagnostic and therapeutic method for identification and treatment of postural disturbances.

BACKGROUND OF THE INVENTION

Postural asymmetries of the human body, generally denoted as "behaviors", affect more than 78% of world population, implying symptoms, and in particular pain, for a large part of the subjects involved. These asymmetries are often related to the generic pathologic condition commonly addressed as "back pain".

In a recent paper appeared on "Lancet", an overview of the impact of chronic back pain in industrial societies is provided. According to such paper, in the United States back pain is the most frequent cause for working ability limitations in subjects under forty-five, the second most frequent reason for medical visits and the third most common reason for surgical interventions. Furthermore, each year about 2% of United States working population receives indemnities from insurance companies due to back pain.

A similar situation can be found in Europe. In particular, back pain is responsible for 12% of working days lost due to illness in Great Britain and for 11% to 20% of lost working days in Sweden.

Up to now, said postural asymmetries have been generically attributed to functional disturbances of the musculo-skeletal system, and rehabilitation and pharmacological treatment have accordingly been used as a remedy. However, in most cases these remedies have proved not able to provide a definitive and satisfactory solution. Furthermore, pharmacological treatment has the important disadvantage of not being tolerable to all subjects.

Recently, the so-called plantar reflexotherapy as been introduced, which consists in the stimulation of particular areas of the foot sole substantially corresponding to the insertion points of the intrinsic muscles responsible for the maintenance of the arcus plantaris. Through such stimulation it is possible to affect the general physiology of the human body for therapeutic purposes. However, potentialities of plantar reflexotherapy have not been fully exploited yet in clinical settings as a tool for routine diagnosis and treatment.

OBJECT AND SUMMARY OF THE INVENTION

The technical problem underlying the present invention is that of providing a method for etiologic diagnosis and for therapeutic treatment of postural disturbances allowing to overcome the drawbacks mentioned above with reference to the known art.

Such problem is solved by a method for etiologic diagnosis of postural disturbances, comprising the steps of:
identifying the type of a patient's postural disturbance to ascertain whether it is of an ascending, descending or multiple type, by means of mechanical maneuvers each apt to inhibit a respective foot or cranial nervous input to the Central Nervous System; and
in case an ascending postural disturbance is identified, identifying the specific intrinsic muscle(s) of the foot sole responsible for such disturbance.

Preferably, the step of identifying the type of postural disturbance in its turn comprises, in a patient having an hypertonic hip rotator muscle, the steps of: positioning the patient's hand controlateral to the rotator hypertone onto the shoulder omolaterali to the hypertone, so as to interrupt inputs coming from the cranial receptors; and positioning the patient's hand omolaterali to the hypertone under the patient's nape, so as to interrupt inputs coming from the foot receptors.

Furthermore, the step of identifying the foot intrinsic muscle(s) responsible for the postural disturbance may comprise the steps of: evaluating a basic force of a chosen muscle, i.e. the deltoid muscle, in an unperturbed condition to establish a force threshold; and evaluating the same force while performing a light tactile stimulation in the insertion point of each intrinsic muscle of the foot sole.

The diagnostic method may also provide for the investigation of breathing and/or deglutition abnormalities.

A further preferable step of the method provides performing an ocular convergence test, which test provides a dynamic phase, wherein a pen or the like is moved towards the patient's face, centrally with respect thereto, up to touch the patient's nose, while the patient's eyes follow the pen or the like throughout its movement, and a static phase, wherein the patient is asked to look at the pen or the like positioned in contact with the patient's nose.

According to the same inventive concept, the invention also provides a therapeutic method for correction of ascending postural disturbances, comprising a step of exteroceptive, pressoceptive, proprioceptive and/or reflexogen stimulation of an insertion point of an intrinsic muscle identified as responsible for a patient's postural disturbance.

Preferably, said therapeutic stimulation is performed by elastic discrete particles arranged at a shoe sole or located inside a plantar, and more preferably arranged at one or more locations selected among adductor hallucis, flexor hallucis brevis, flexor digiti quinti brevis, abductor digiti quinti, cuneus supinator, cuneus pronator and abductor hallucis.

The present invention also provides a combination of a method for etiologic diagnosis of ascending postural disturbances and of a therapeutic method for correction of such ascending postural disturbances, comprising the steps of:
identifying the type of a patient's postural disturbance to ascertain whether it is of an ascending, descending or multiple type, by means of mechanical maneuvers each apt to inhibit a respective foot or cranial nervous input to the Central Nervous System;
in case an ascending postural disturbance is identified, identifying the specific intrinsic muscle(s) of the foot sole responsible for such disturbance; and
performing an exteroceptive, pressoceptive, proprioceptive and/or reflexogen stimulation of an insertion point of the intrinsic muscle(s) identified as responsible for the ascending postural disturbance.

In the present context, the expression "postural disturbance" is to be understood in a wide sense as comprising all types of musculo-skeletal asymmetries, muscle hypotone or hypertone, eventually associated with localized pain.

The present invention provides some relevant advantages. The main advantage lies in the fact that the diagnostic method of the invention allows reliable functional diagnosis to be carried out routinely in a clinical setting. In its turn, the therapeutic method of the invention allows functional recover—as opposed to "rehabilitation"—without the need for pharmacological treatment.

Other advantages, features and steps of the present invention will be made apparent in the detailed description of

DETAILED DESCRIPTION

The diagnostic and therapeutic methods of the invention move from the observation, made as a necessary preliminary phase to said methods, that the tone of the so-called intrinsic muscles of the foot sole influences the postural behavior of the whole body in both static and dynamic conditions. In particular, as explained in detail in the following, a clinical study was carried out showing that an altered podalic rest determines abnormal signals inputted by the nervous terminations of the foot to the Central Nervous System. Such abnormal input signals cause, in their turn, altered control signals outputted from said System, i.e. an abnormal control of the musculoskeletal segments of the whole body.

More specifically, the clinical study carried out showed that a normal tone of the foot intrinsic muscles and an associated normal elasticity of ligaments, tendons, plantar aponeuroses and articular capsules determined a normal, physiological posture of the whole body. On the contrary, an altered podalic rest, e.g. flat or cave foot of various severeness, pronated or supinated foot, valgus or varus foot, caused alterations in the spatial position of the skeletal segments and situations of functional overload on one or more articulations of the body.

Such altered podalic rest was mostly due to hypotone of one or more of the foot intrinsic muscles, which were not able to maintain normal bone arcades either in static or dynamic conditions.

As it is well-known for the person skilled in the art, the mio-fascial and capsular structures of the foot have many autonomous nervous terminations of a pressoceptive, exteroceptive and proprioceptive type. Such terminations involuntarily input information to the Central Nervous System, at both cranial and spinal level, about terrain conditions.

Accordingly, in said preliminary phase of the method of the invention it was observed that foot nervous terminations did not function properly when enveloped in hypo- or hypertonic muscular structures, in fascial structures having low elasticity because too tense or too relaxed, or in capsular structures having spacings not perfectly preserved and therefore functionally overloaded.

As mentioned above, due to such improper operation of the foot nervous terminations abnormal inputs are fed to the Central Nervous System. As a consequence, the Central Nervous System provides altered outputs towards the anti-gravitational system of the human body, i.e. towards the structures allowing the maintenance of the standing posture (the so-called static chain). In particular, disharmonic distribution of muscular tone and of fascial, tendineous and capsular elasticity of the body structures deputed at developing the anti-gravitational force were observed. Such disharmonic distribution along the static chain of the human body determined a chronic, asymmetric contraction of large superficial muscular masses, like deltoid, scaleno, posterior rectus and gluteus, that should instead be used to perform a dynamic gesture only and, after that, return in a resting condition, as well as an alteration of articulations' spatial distribution.

Specific examples of resulting altered postures were lower torso, head and/or shoulder asymmetries, spacing abnormalities at the ankles, knees or hips, spine curve alterations both on the frontal plane, e.g. lateral deviations and idiopathic scolioses, and on the sagittal plane, e.g. hyperlordoses, hypercyphosis, verticalizations of the lumbar and/or cervical segments and inversions of the physiological curves. All these conditions brought articular pain that might become disabling.

The above observations therefore indicated that the foot is not to be considered as a simple resting structure, but instead as a true nervous sensorial organ.

The muscles or regions of the foot that were identified as the sole responsible for the maintenance of the normal static bone arcades, and therefore of a whole body normal posture, are essentially seven, i.e.:

flexor hallucis brevis,
adductor hallucis,
flexor digiti quinti brevis,
abductor hallucis,
abductor digiti quinti,
cuneous pronator, and
cuneous supinator.

The last two cuneous belong to the Achilleous-Calcaneous system and consist almost exclusively of fascial tissue, comprising also the proximal insertions of plantar aponeuroses.

On the basis of the above considerations, the general inventive concept of the present invention lies in the fact that the foot muscles/regions from which the abnormal ascendant information to the Central Nervous System originates are identified through diagnosis and then intervened upon through therapy.

A specific example of implementation of the diagnostic method of the invention will now be described.

According to a first step of the method, the type of a postural disturbance of a patient is to be identified. Specifically, it is investigated whether such postural disturbance depends upon the foot, i.e. it is of an ascendant type, upon the cranial receptors, i.e. it is of a descendent type, or upon both foot and cranial receptors, i.e. it is of a multiple type.

In case of a postural disturbance at one or more of the hip rotator muscles, a specific test is herein provided for carrying out said type identification.

Assuming the patient presents an hypertone at the hip rotator(s), in a first phase of the test the patient's hand contro-lateral to the hypertone is positioned onto the shoulder omolaterali to the rotator hypertone, so as to interrupt inputs coming from the cranial receptors. For example, in a patient with hypertone at the right rotator, the left hand is to be positioned onto the right shoulder. If the hypertone disappears, then it is concluded that the disturbance is of a descending type.

In a second phase of the test, the patient's hand omolaterali to the muscle hypertone is positioned under the nape. For example, in a patient with hypertone at the right rotator, the right hand is to be positioned under the nape. If the hypertone disappears, then it is concluded that the disturbance is of an ascending type.

If the hypertone disappears in both cases, the disturbance is of a multiple type.

The hip test just described can be generalized for investigating the causes for a muscle hypertone in any district of the human body, and in particular at the upper and lower limbs. In the general case, the test will still comprise two separate phases, one providing inhibition of the nervous inputs coming from the cranial receptors and the other of the nervous inputs coming from the foot receptors. In both cases such inhibition will be obtained by a respective mechanical maneuver.

It will be appreciated that in the case of the hip rotator muscles just described, the method of the invention is of a very simple implementation.

In case the first step has identified a postural disturbance of an ascending type, a second neurological step of the diagnostic method allows for the identification of the specific muscle(s) of the foot sole responsible for such disturbance.

In particular, this second step relates the function of the cutaneous exteroceptors in the area of insertion of each intrinsic muscle of the foot sole with the force of the musculo-skeletal structure affected by the postural disturbance or with the force of a sample muscle.

According to a specific implementation of this second step, a sample muscle is selected, e.g. the deltoid muscle. Then, the basic force thereof is evaluated in an unperturbed condition, i.e. without any kind of stimulation, in order to establish a base force threshold.

In a successive phase, said force is evaluated again while performing a light tactile stimulation in the insertion point of each intrinsic muscle of the foot sole.

If the sample muscle force stays strong, i.e. its force remains substantially unchanged with respect to said threshold, it is concluded that the stimulated foot intrinsic muscle operates correctly and does not need stimulation. On the contrary, if the sample muscle weakens, it is concluded that the stimulated foot sole muscle does not operate correctly and needs therapeutic stimulation.

Those skilled in the art will understand that the second step of the diagnostic method just described is a modified challenger test. In particular, this second step consists of a classic kinesiologic test of applied kinesiology according Goodheart which is related to the insertion point of each single intrinsic muscle of the foot sole contributing to the maintenance of the static normal plantar arcades. The test can be regarded as corresponding to neurological tests such those associated with patellar or ulna reflex.

As important additional steps of the diagnostic method of the invention, breathing and deglutition are also investigated.

In fact, as it is known to those skilled in the art, physiological breathing has to take place through nasal choanas and in a perfectly symmetrical way. This allows a symmetrical development of the face, a correct drainage of auricular ducts and a normal tongue operation.

On the contrary, asymmetric breathing, i.e. with a nostril more dilated than the other, causes an abnormal expansion of frontal and zygomatic sinus, with the risk of nasal septum deviations, recidivate otitis and facial asymmetry.

Furthermore, as it is also known to those skilled in the art, an oral breathing determines alterations in both face development and tooth distribution, especially in the upper arcade, the formation of ogival bone palate, and possible effects also on the mobility of the mandible.

Finally, also the use of the muscles deputed to breathing function, i.e. diaphragm and intercostal muscles, is very important, as opposed to using the so-called accessory breathing muscles, i.e. scalenus, sternocleidomastoideus, trapezius, grande and small pectoral, grande and small dorsalis, as the use of these latter muscles determines asymmetries in the scapular girdle and pain of the scapularomeral girdle which often are confused for periarthritis or neck pain.

Similarly, as far as deglutition is concerned, it is known that physiologic deglutition takes place by positioning the tongue apex on the papilla between the two upper median incisors. This allows for a homogenous and perfectly linear eversion movement of the tongue which transmits to the muscles above and under the hyoid bone and, consequently, to all muscles and neck structures.

An abnormal deglutition, i.e. the positioning of tongue apex between teeth or at the lower median incisors, determines instead a tongue eversion movement of a torsional type which affects the other musculo-skeletal structures involved.

Notwithstanding the fact that the above effects of abnormal breathing and deglutition onto related musculo-skeletal structures were already known, such functions has never been related to body posture disturbances.

In a preliminary phase of the diagnostic method of the invention, instead, an abnormal deglutition has been related to torsion of hyoid bone, demonstrating it by a CAT dynamic examination, and also to functional nodules of vocal cords and to dislalie.

The aforementioned additional steps of the present diagnostic method provide analysis of breathing and deglutition, in order to investigate possible postural alterations related thereto.

A further additional step of the diagnostic method of the invention provides for the analysis of ocular convergence by means of a convergence test having a static and a dynamic phase.

Normally, medical doctors analyze ocular mobility by progressively moving an object, typically a pen, towards the patient's face up to a distance of about 5–6 cm from the nose tip, while the patient follows the object with his/her eyes.

However, in a preliminary step of the diagnostic method of the invention it was observed that significant variations of ocular convergence happens just within said distance of 5–6 cm from the patient's face that known-art tests do not take into consideration. Accordingly, the present invention also provides a test for ocular convergence, which will be from now on denoted as extreme convergence test.

A first, dynamic phase of such test provides that an object, preferably a pen or the like, is moved towards the patient's face, centrally with respect thereto, up to touch the patient's nose, while the patient's eyes follow the object throughout its movement.

In a second, static phase of the test the object is positioned in contact with the patient's nose tip while asking the patient to look in front of him/her. Then, the patient is asked to look at the object.

If, in said dynamic and static phase, both eyes converge at the inner medial corner of the orbits, a normal convergence is diagnosed. If, instead, one or both eyes converge only partially, blocking their excursion in the middle of the orbit, an hypo-convergence is diagnosed. Finally, if one or both eyes diverge laterally, a divergence is diagnosed.

The extreme convergence test just described allows identifying possible hypotonies at the oculo-motor muscles, which hypotonies account for eye tiredness and tearing, photophobias and low capacity of evaluating spacing between objects.

It will be appreciated that the method for etiologic diagnosis of the invention is particularly important in clinical examinations carried out upon pediatric patients.

It will be also understood that the diagnostic method of the invention allows identification of the "primum movens" of various alterations that are today regarded as "behaviors" and of all pathologies presently addressed by generic and descriptive expressions such as "back pain".

The therapeutic method of the invention will now be described.

This method consists in a therapeutic treatment for ascending postural anomalies, directed to correction of abnormal signals inputted to the Central Nervous System by the hypotonic muscle(s) of the foot sole identified as responsible for the patient's postural disturbance by the diagnostic method described above. In particular, the method provides exteroceptive, pressoceptive, proprioceptive and/or reflexogen stimulation of the insertion point(s) of such intrinsic muscle(s).

Said stimulation can be effected manually, but can also advantageously be performed by elastic discrete particles providing a return elastic force of the same entity of the force applied thereon. Clinical testing revealed that substantially irregularly shaped particles made of natural rubber and/or Para rubber, preferably completely non-allergenic, provide optimal stimulation results.

The aforementioned stimulating particles can be housed inside swellings or alveoli applied onto a plantar or directly onto a shoe sole. The external layer of such swellings or alveoli can be made of a material suitable to be in contact with the foot sole and soft to the touch, such as alkantara, which also assures resistance to wear.

Alveoli or swellings should of course be located, depending on the specific diagnosis, at adductor hallucis, flexor hallucis brevis, flexor digiti quinti brevis, abductor digiti quinti, cuneus supinator, cuneus pronator and abductor hallucis.

This particular implementation of the therapeutic method of the invention allows stimulating continuously for hours the patient without annoying him/her.

Furthermore, said particles can provide a constant stimulation force for at least one year.

The idea of providing elastic and soft materials originates from the need for making the foot sole "deaf" to both rigid terrain and shoe soles. In fact, although it is true that the feet have to act as sensors and have to sense terrain diversities and informing accordingly the Central Nervous System, it is also true that walking on uniformly rigid terrain reduces receptor sensitivity.

For ascending postural disturbances, the therapeutic method of the invention allowed to eliminate symptoms, bringing back to a physiological status the spatial position of the skeletal segments previously altered and painful, also at the radiological exam, particularly for back pain.

Two specific examples of application in a clinical setting of the diagnostic and therapeutic method of the invention will now be described.

A population sample of 125 subjects aged between 20 and 86 (82 females and 43 males) and of 16 subjects in pediatric age (age 8 to 12, 11 females and 5 males) having a verticalization of the cervical section of the spinal column and neck pain was taken into consideration. This population sample was selected by ruling out traumatic cases or systemic etiologies.

All the subjects underwent a global postural exam, with X-rays of the entire spinal column in orthostatism, taking antero-posterior and latero-lateral views.

The nature of the postural disturbance was diagnosed as of an ascending type and the foot hypotonic muscles responsible for the disturbance were identified by the diagnostic method of the invention.

All the subjects showed chronic monolateral tension of the trapezius muscle with the head reclining laterally. The most frequent symptoms were represented by a sensation of heaviness at the base of the neck and pains, mainly unilaterally, with exacerbations radiating to the posterior face of the skull till its vertex. There was also a high incidence of tension headaches, in about 45% of the examined subjects. The incidence of vertigo was about 30%.

All the subjects were treated by proprioceptive stimulation, using plantars of the type described above.

Five clinical follow-up examinations were performed in the course of the subsequent twelve months. These follow-ups showed that the painful symptoms became less intense already in the first month of treatment. The other symptoms were progressively attenuated and disappeared completely when the 3D spatial arrangement of the cervical vertebrae had returned to the physiological lordosis, which occurred in 78% of the patients.

In particular, the episodes of tension headache and vertigo regressed after a variable period of increase in the spontaneous accesses in 80% of the treated subjects.

In a second experimental study, a population sample of 69 subjects, aged between 12 and 48 (40 females and 29 males) was analyzed. All subjects in the sample exhibited an asymmetrical spatial arrangement of the pelvis, with asymmetry of the iliac crests, of the SIAS and of the posterior holes of the pelvis. The patients suffered from different painful symptoms, affecting above all the lumbar area. Five of them, 2 females and 3 males, practiced some sports, in a non professional way and suffered occasionally, in addition to lumbar pains, from pubis' pains, too.

All subjects underwent a radiography of the entire vertebral column in antero-posterior and latero-lateral projection in orthostatism, with record of the examination on the millimetered plate, a radiography of the pelvis in antero-posterior projection in orthostatism and a 3D VRS Formetric's examination.

Subjects were diagnosed ascending postural disturbance by the diagnostic method of the invention.

Subjects were then divided into three groups of therapeutic treatment, as detailed in the following.

Group A—27 subjects, 15 females and 12 males, aged between 12 and 48, were treated by placing a traditional wedge under the heel corresponding to the downwards displaced hemipelvis. At the beginning of treatment, 19 subjects (corresponding to about 70.3% of the sample), 13 females and 6 males, exhibited a pelvis asymmetry with left iliac crest with upwards displacement rising from a minimum of 5 mm to a maximum of 16 mm, while 8 subjects (corresponding to about 29.6% of the sample), 2 females and 6 males, exhibited a pelvis asymmetry with right iliac crest with upwards displacement rising from a minimum of 3.5 mm to a maximum of 16 mm. The thickness of the wedge was lightly thinner than the pelvis' asymmetry, i.e. for a left hemipelvis with a downwards asymmetry of 1 cm, a wedge 0.5 cm thin was placed under the left heel.

Follow-ups for checking the spatial arrangement of the pelvis and of the vertebral column were performed just after placing the wedge, after one month and after three months of treatment.

Group B—15 subjects, 10 females and 5 males, aged between 12 and 48, didn't undergo any treatment and were used as control's group. Follow-ups were performed at the same times of Group A.

Group C—27 subjects, 15 females and 12 males, aged between 12 and 48, were treated by the proprioceptive stimulation according to the therapeutic method of the invention, after identification of the hypotonic foot intrinsic muscles responsible for their postural disturbances according to the diagnostic method of the invention. Also for Group C, follow-ups were performed at the same times of the other groups.

The results of the study are summarized in the following.

Group A—The use of a monolateral wedge under the heel corresponding to the more downwards displaced iliac crest constantly caused, in all subjects, greater derangement affecting the entire vertebral column and in particular the dorsal part of it. A more careful analysis of the radiographic plate in antero-posterior projection done with or without placing the wedge under the heel showed the same alterations that have been recorded by the 3D VRS Formetric examination. Anyway, the posturographic examination didn't show a normalization of the weights' distribution, as shown by the recordings of the plantar stance images barefoot or with the monolateral wedge.

Group B—Subjects didn't undergo any therapeutic treatment, and no changes in the tests' outcome or symptoms were obtained.

Group C—Subjects underwent a constant increasing improvement of the painful symptoms and a better realignment, both of the pelvis and of the vertebral column. Even the posturographic examination performed through the specific plantar stimulation, that means according to the patients' disorder, showed already at the beginning of treatment a more uniform distribution of the weight between both feet and between the fore and back foot.

The results of this trial experimentation indicated that the use of merely mechanical tools, such as monolateral wedges, with the aim to correct a highly complex situation such as a pelvis' asymmetry, was unsuitable. In particular, each therapeutic treatment on the pelvis produced consequences on the vertebral column and consequently on the whole organism. Accordingly, the use of monolateral lifting wedges placed under the heel corresponding to the downwards displaced hemipelvis of an asymmetrical pelvis with a false asymmetry of the lower limbs, proved to be a non-efficient therapy, both theoretically, because it was not based on the principles ruling the physiology of our organism, and practically, because it caused spine's derangement.

On the contrary, the proprioceptive therapy according to the invention achieved the correction of the bilateral plantar stance and the recovery of the tone intrinsic muscles of the foot's sole, by restoring the balance of the pelvis' both in frontal and in lateral projection, without exerting any damaging consequence on the entire vertebral column.

The inventor noticed that also in non-evolutive idiopathic scoliosis it is possible to arrive to an etiologic diagnosis for the presence of a primary functional alteration at the foot sole muscles and at oculo-motor muscles. The treatment aimed at functional recover of these two structures assured optimal results verified by radiographic examinations and the de-rotation of the vertebrae involved.

It also be appreciated that stimulation of intrinsic muscles is important also for the vascular system. In fact, as it is well-known for those skilled in the art, the foot is also a peripheral vascular organ originating the so-called "vis a tergo" or peripheral thrust which represents the mechanical propulsion allowing for venous and lymphatic return at the lower limbs. In particular, the generation of an anti-gravitational propulsive force to obtain the so-called back flow of the blood is due not only to the contraction of the twin muscles of the shanks, but primarily by a normal elasticity of the plantar arcades that during walking deform and eject blood out of the venous region of Legjan positioned at the foot sole. Also for this function, identifying and intervening onto the foot musculo-ligamentous structures in hypotone allows to bring back to normality the pumping action, by eliminating both subjective symptoms, e.g. leg heaviness sensation and swelling, and capillary or venous ectasie, teleangectasie and varici.

It will be appreciated at this point that the method of the invention allows a simple etiologic diagnosis of musculo-skeletal disturbances and a related physiologic therapy.

The present invention has been hereto described with reference to preferred embodiments thereof. It is understood that other embodiments might exist, all falling within the concept of the same invention, and all comprised within the protective scope of the claims hereinafter.

What is claimed is:

1. A method for etiologic diagnosis of postural disturbances, comprising the steps of:
    identifying the type of a patient's postural disturbance to ascertain whether it is of an ascending, descending or multiple type, by means of mechanical maneuvers each apt to inhibit a respective foot or cranial nervous input to the Central Nervous System; and
    in case an ascending postural disturbance is identified, identifying the specific intrinsic muscle(s) of the foot sole responsible for such disturbance,
    wherein said step of identifying the type of postural disturbance in its turn comprises, in a patient having hypertonic hip rotator muscle, the steps of:
        positioning the patient's hand contralateral to the rotator hypertone onto the shoulder homolateral to the hypertone, so as to interrupt inputs coming from the cranial receptors; and
        positioning the patient's hand homolateral to the hypertone under the patient's nape, so as to interrupt inputs coming from the foot receptors.

2. The diagnostic method according to claim 1, wherein said step of identifying the foot intrinsic muscle(s) responsible for the postural disturbance in its turn comprises the steps of:
    evaluating a basic force of a chosen muscle in an unperturbed condition to establish a force threshold; and
    evaluating the same force while performing a light tactile stimulation in the insertion point of each intrinsic muscle of the foot sole.

3. The diagnostic method according to claim 2, wherein said chosen muscle is the deltoid muscle.

4. The diagnostic method according to claim 1, comprising a further step of investigating breathing abnormalities.

5. The diagnostic method according to claim 1, comprising a further step of investigating deglutition abnormalities.

6. The diagnostic method according to claim 1, comprising a further step of performing an ocular convergence test, which test provides a dynamic phase, wherein a pen or the like is moved towards the patient's face, centrally with respect thereto, up to touch the patient's nose, while the patient's eyes follow the pen or the like throughout its movement, and a static phase, wherein the patient is asked to look at the pen or the like positioned in contact with the patient's nose.

7. A combination of a method for etiologic diagnosis of ascending postural disturbances and of a therapeutic method for correction of such ascending postural disturbances, comprising the steps of:
    identifying the type of a patient's postural disturbance to ascertain whether it is of an ascending, descending or multiple type, by means of mechanical maneuvers each apt to inhibit a respective foot or cranial nervous input to the Central Nervous System;
    in case an ascending postural disturbance is identified, identifying the specific intrinsic muscle(s) of the foot sole responsible for such disturbance; and
    performing an exteroceptive, pressoceptive, proprioceptive and/or reflexogen stimulation of an insertion point of the intrinsic muscle(s) identified as responsible for the ascending postural disturbance, wherein said step of identifying the type of postural disturbance in its turn comprises, in a patient having a hypertonic hip rotator muscle, the steps of:

positioning the patient's had contralateral to the rotator hypertone onto the shoulder homolateral to the hypertone, so as to interrupt inputs coming from the cranial receptors; and positioning the patient's hand homolateral to the hypertone under the patient's nape, so as to interrupt inputs coming from the foot receptors.

8. The combination of a method for etiologic diagnosis of ascending postural disturbances and of a therapeutic method for correction of such ascending postural disturbances according to claim 7, wherein said stimulation of said therapeutic method is performed by elastic discrete particles arranged at a shoe sole.

9. The combination of a method for etiologic diagnosis of ascending postural disturbances and of a therapeutic method for correction of such ascending postural disturbances according to claim 7, wherein said stimulation of said therapeutic method is performed by elastic discrete particles located inside a plantar.

10. The combination of a method for etiologic diagnosis of ascending postural disturbances and of a therapeutic method for correction of such ascending postural disturbances according to claim 8 or 9, wherein said particles are retained inside alveoli arranged at one or more locations selected among adductor hallucis, flexor hallucis brevis, flexor digiti quinti brevis, abductor digiti quinti, cuneus supinator, cuneus pronator and abductor hallucis.

* * * * *